United States Patent
Suzuki et al.

(10) Patent No.: US 9,623,154 B2
(45) Date of Patent: *Apr. 18, 2017

(54) HEAT-SHRINKABLE TUBE HAVING TEARABILITY

(71) Applicant: JUNKOSHA INC., Kasama-shi, Ibaraki (JP)

(72) Inventors: Masahiro Suzuki, Tokorozawa (JP); Kohei Yuri, Mito (JP); Masaru Miyoshi, Mito (JP)

(73) Assignee: Junkosha Inc., Ibaraki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/205,560

(22) Filed: Jul. 8, 2016

(65) Prior Publication Data

US 2016/0317716 A1  Nov. 3, 2016

Related U.S. Application Data (63) Continuation of application No. 14/348,309, filed as application No. PCT/JP2012/080520 on Nov. 19, 2012, now Pat. No. 9,446,171.

(30) Foreign Application Priority Data

Nov. 21, 2011 (JP) .................. 2011-245074

(51) Int. Cl.
 *B29D 22/00* (2006.01)
 *A61L 29/14* (2006.01)
 (Continued)

(52) U.S. Cl.
 CPC ............ *A61L 29/14* (2013.01); *A61L 29/041* (2013.01); *A61L 29/049* (2013.01);
 (Continued)

(58) Field of Classification Search
 CPC .... A61L 29/041; A61L 29/085; A61L 29/049; A61L 29/14; Y10T 428/1331
 (Continued)

(56) References Cited

U.S. PATENT DOCUMENTS

| | | |
|---|---|---|
| 4,029,868 A | 6/1977 | Carlson |
| 2012/0010369 A1 | 1/2012 | Iizuka et al. |

FOREIGN PATENT DOCUMENTS

| | | |
|---|---|---|
| JP | 03-212441 | 9/1991 |
| JP | 08-012767 | 1/1996 |

(Continued)

OTHER PUBLICATIONS

Fluon ETFE Product Information Sheet, AGC Chemicals Americas, Inc., Dec. 2010.*

(Continued)

*Primary Examiner* — Ellen S Wood
(74) *Attorney, Agent, or Firm* — THe Webb Law Firm (57) ABSTRACT

An object of the present invention is to provide a tube which can be easily torn and has a large heat-shrinkability at a low temperature. The tube of the present invention is a heat-shrinkable tube having tearability, including a mixture of a fluorine resin and a different kind of resin from the fluorine resin, in which an amount of change in loss energy, $\Delta E$ loss, with change in temperature from 175° C. to 185° C. is a positive value.

7 Claims, 5 Drawing Sheets

(51) Int. Cl.
    *A61L 29/04*       (2006.01)
    *A61L 29/08*       (2006.01)

(52) U.S. Cl.
    CPC ......... *A61L 29/085* (2013.01); *A61L 2400/00* (2013.01); *Y10T 428/1331* (2015.01)

(58) Field of Classification Search
    USPC .............................................. 428/34.7, 35.1
    See application file for complete search history.

(56) References Cited

FOREIGN PATENT DOCUMENTS

| | | |
|---|---|---|
| JP | 08-216252 | 8/1996 |
| JP | 09-031285 | 2/1997 |
| JP | 2002-012731 | 1/2002 |
| JP | 2007-179889 | 7/2007 |
| JP | 2007-321817 | 12/2007 |
| JP | 2008-020037 | 1/2008 |

OTHER PUBLICATIONS

International Search Report, Date of Mailing Jan. 22, 2013.
PCT/ISA/237 of PCT/JP2012/080520 and partial English translation.
English translation of International Preliminary Report, Date of completion: Jan. 7, 2014.
Melt-Processable Dupont Teflon Fluoroplastics Resins, Product Information.

\* cited by examiner

HEAT-SHRINKABLE TUBE HAVING TEARABILITY

CROSS-REFERENCE TO RELATED APPLICATIONS

This application is a continuation of U.S. patent application Ser. No. 14/348,309, filed Mar. 28, 2014, which is the U.S. national stage application of PCT Application No. PCT/JP2012/080520, filed Nov. 19, 2012, which claims priority to Japanese Patent Application No. 2011-245074, filed Nov. 21, 2011.

TECHNICAL FIELD

The present invention relates to a heat-shrinkable tube having tearability which is made of a fluorine resin, and more particularly to a tearable tube having heat shrinkability in which a material of the tube is a thermoplastic fluorine resin.

BACKGROUND ART

A tearable tube has been used as a protective member for various articles until the articles are used. Among them, a tearable tube made of a fluorine resin has properties such as heat resistance, chemical resistance, water and oil repellency, non-adhesion, self-lubricity or the like which cannot be obtained with a tearable tube made of hydrocarbon-based synthetic resin.

Therefore, by using these properties, the tube has been used as a protective tube for precision equipment, electronic components or the like, or as a tube for introducing medical devices, which is used to introduce a catheter, a guide wire or the like into a body. The tube for introducing medical devices is unnecessary after a catheter or the like is introduced into the body, and also there is a management problem for maintaining the hygienic state. Thus, after the catheter is introduced into the body, the tube has to be withdrawn while being torn.

A tearable tube is required to securely protect the device mounted inside thereof, to be easily tearable without using a special device, and to maintain the properties possessed by the fluorine resin. The conventional tube in which a cut was made on its surface along with the longitudinal direction was not easily torn. Thus, in Japanese Patent Application Laid-Open No. 2008-20037, in order to easily tear without a need for an excessively cut portion, there has been proposed an extruded tube made of a fluorine resin which is obtained by extrusion molding a mixture of a tetrafluoroethylene resin and a fluorine resin having a low molecular weight. In order to coat the surface of a device such as a catheter with a fluorine resin, the heat-shrinkable tube made of a fluorine resin is needed to be heat-shrank by heating the tube after coating its surface. However, when the shrinkage of the heat-shrinkable tube is small, there is a problem that the close contact between the heat-shrinkable tube and the device is insufficient and also workability is deteriorated.

SUMMARY OF THE INVENTION

An object of the present invention is to provide a tearable tube made of a fluorine resin, which can be easily torn, has a large heat-shrinkability, can be ensured to be close contacted and coated by heat shrinking when the tube is mounted in a device, and also can be simply torn at time when the device is used.

The object of the present invention can be achieved by a heat-shrinkable tube (1) having tearability, which includes a mixture of a fluorine resin and a different kind of resin from the fluorine resin, in which when a sine vibration stress with a cycle of 30 sec and an amplitude of 10 g is applied and a temperature is raised at rate of 5° C./min, an amount of change in loss energy, $\Delta E$ loss, with change in temperature from 175° C. to 185° C. is a positive value.

In the tube (1), better tearability and heat-shrinkability can be obtained by a tube (2) having a $\Delta E$ loss of 0.05 μJ or more.

In the tube (1), better tearability and heat-shrinkability can be obtained by a tube (3) having a storage elastic modulus at 50° C. of 100 MPa or less.

The object of the invention can be achieved by a heat-shrinkable tube (4) having tearability, which includes a mixture of different kinds of fluorine resins, in which a main fluorine resin is a polymer made of at least three kinds of monomers and contains at least a tetrafluoroethylene and a hexafluoropropylene as constituent monomer units.

In the tube (4), better tearability and heat-shrinkability can be obtained by a tube (5) in which the main fluorine resin contains at least a tetrafluoroethylene, a hexafluoropropylene and a perfluoroalkylvinyl ether as constituent monomer units.

In the tube (4), better tearability and heat-shrinkability can be obtained by a tube (6) in which the main fluorine resin contains at least a tetrafluoroethylene, a hexafluoropropylene and a vinylidene fluoride as constituent monomer units and has a glass transition temperature is 40° C. or higher.

In the tube (4), better tearability and heat-shrinkability can be obtained by a tube (7) in which a fluorine resin other than the main fluorine resin contains at least a tetrafluoroethylene-ethylene copolymer or a polyvinylidene fluoride.

In the tube (4), better tearability and heat-shrinkability can be obtained by a tube (8) in which a mixing ratio of the main fluorine resin and a resin other than the main fluorine resin is from 98:2 to 70:30 by mass ratio.

The object of the present invention can be achieved by a heat-shrinkable tube having tearability which contains a tetrafluoroethylene-hexafluoropropylene-perfluoroalkylvinyl ether copolymer as a main component and further contains a tetrafluoroethylene-ethylene copolymer. In the tube, the mixing ratio of the tetrafluoroethylene-hexafluoropropylene-perfluoroalkylvinyl ether copolymer and the tetrafluoroethylene-ethylene copolymer is from 98:2 to 70:30 by mass ratio.

The tearable tube made of the fluorine resin of the present invention has good heat-shrinkability at a low temperature of about 200° C. along with tearability, so that the tube may be mounted tightly on a mounting member when the tube is provided in a device, and may be excellent in handlability. Further, the tearable tube made of the fluorine resin of the present invention can be manufactured by melt-extruding a raw material blended with different kinds of thermoplastic fluorine resins, so that the tearable tube made of the fluorine resin which is easily produced and has a stable tear characteristics may be obtained.

DETAILED DESCRIPTION OF THE INVENTION

A heat-shrinkable tube having tearability is disclosed in Japanese Patent Application Laid-Open No. 2008-20037. However, the thermal shrinkage (a change rate of the inner diameter) of the disclosed tube therein is 30% at most, and this cannot be said to be sufficient.

As for the tube of the present invention, a thermal shrinkage at a low temperature of about 200° C. may be 40% or more, and ΔE loss>0 is important for that. The aggregation structure of molecular chain which could not be collapsed near the glass transition temperature (at a low temperature side) will be released gradually at a high temperature side of 1.50° C. or higher, so that strain of the object due to an external force becomes larger. "ΔE loss>0" means that the increase of such strain is led to an increase in loss energy at the high temperature side. Further, from another perspective, it means that in the tube of the present invention, the molecules may move freely to some extent while maintaining a certain degree of entanglement between the molecules even at around 200° C. It is considered that when the tube is heated to around 200° C., it is easy to return to the state of the molding due to such properties, and thus, high shrinkage ratio may be obtained. Here, the ΔE loss means an amount of change in loss energy with change in temperature from 1.75° C. to 185° C. when a sine vibration stress is applied and a temperature is raised at rate of 5° C./min. The measurement sample is not the tube as it is, but is obtained by hot melt pressing the tube. Since the measurement sample is subjected to thermal hysteresis, measurement is performed to obtain a change in loss energy at around 180° C. at a lower temperature side instead of the change in loss energy at around 200° C. where the heat shrink is performed. The conventional tubes take ΔE loss of a negative value. In such conventional products, since the entanglement of molecular chains is almost missing at a high temperature side of 150° C. or higher, an action of return to the state at the time of Molding hardly occurs, and as a result thermal shrinkage is low. When ΔE loss is 0.05 μJ or more, it is preferred in that higher thermal shrinkage may be Obtained. When ΔE loss is 0.2 μJ or more, it can be said to be a more preferred embodiment. AE loss is highly dependent on the characteristics of a "main fluorine resin" to be described later.

The heat-shrinkable tube having tearability of the present invention would be expanded after molding the tube. If the elastic modulus is too high at that time, the tube may return to its original size momentarily even though the tube is expanded. As a result, a high expansion ratio is hardly obtained, and thus, a high thermal shrinkage is hardly obtained as well. The elastic modulus at 50° C. is preferably 100 MPa or less.

As a material of the main fluorine resin in which the thermal shrinkage is large at a low temperature of 200° C., a tetrafluoroethylene-hexafluoropropylene-perfluoroalkyl vinyl ether copolymer is exemplified. The main fluorine resin as mentioned herein means a resin having the highest mixing ratio among a plurality of different kinds of fluorine resins. The above mentioned copolymer is a terpolymer obtained by adding a perfluoroalkyl vinyl ether monomer in a monomer constituting a tetrafluoroethylene-hexafluoropropylene copolymer (FEP). The perfluoroalkyl vinyl ether moiety is closely intertwined with other molecules to form an aggregation structure of molecular chain. By the aggregation structure of molecular chain, when the structure is heated to 200° C. in an expanded state at 100° C. after molding, the force to return to the size at the time of molding is applied. Here, from the viewpoint whether an appropriate aggregation structure of molecular chains is generated, the glass transition temperature (Tg) of the tetrafluoroethylene-hexafluoropropylene-perfluoroalkyl vinyl ether copolymer is preferably 68° C. or higher. On the other hand, as for the material having similar composition, the one obtained by blending a tetrafluoroethylene-perfluoroalkyl vinyl ether copolymer with a binary copolymer of a tetrafluoroethylene and a hexafluoropropylene may be considered. However, the entanglement at a molecular level does not occur just only by blending the copolymers, and thus, the effect of preventing rupture at the time of high expansion cannot be expected.

The other materials of the main fluorine resin include a ternary copolymer (THV) of a tetrafluoroethylene, a hexafluoropropylene and a vinylidene fluoride (VDF). The THV is a terpolymer obtained by adding further VDF to monomers constituting the FEP, the VDF portion thereof is greatly polarized into positive and negative, and forming of the aggregation structure of molecular chain starts from this portion. By the aggregation structure of molecular chain, when the structure is heated to 200° C. from an expanded state at 100° C. after molding, the force to return to the size at the time of molding is applied. However, in the case of the THV, the glass transition temperature (Tg) needs to be 40° C. or higher. It is more preferable that the Tg is 45° C. or higher. If the Tg is 40° C. or lower, the aforementioned proper aggregation of molecular chain structure is not made and thus the sufficient thermal shrinkage cannot be obtained. For example, as seen in that THV221 manufactured by Dyneon of 3M Group has Tg of 5° C., and THV610 manufactured by Dyneon of 3M Group has Tg of 34° C., Tg of conventional THV has become lower. In the case of the THV, if the proportion of the tetrafluoroethylene is increased, Tg tends to increase.

A quaternary copolymer (quaternary THV) of tetrafluoroethylene-hexafluoropropylene-vinylidene fluoride-perfluoroalkyl vinyl ether also tends to be similar to THV.

As described above, in the case of ternary or higher polymers, the aggregation structure of molecular chain may be easily made, and thus, the object of the present invention may be achieved.

It is not clear why the heat-shrinkable tube made of fluorine resin having a high shrinkage and excellent characteristics is obtained by blending the ternary (quaternary') copolymer containing fluorine as in the present invention. However, the perfluorovinyl ether component (PVE) in a ternary copolymer, for example, in a tetrafluoroethylene-hexafluoropropylene copolymer increases the entanglement of molecules. Thus, it is believed that the heat-shrinkable tube is less likely to be ruptured even when the tube highly expanded and this is one of the causes.

Further, as reviewed with respect to the reason why the tube having tearability which has excellent characteristics can be obtained by the present invention, it is considered that the reason is the difference between the lengths of the C—F bonds or C—H bonds in the molecule of each of different kinds of fluorine resins, or due to the compatibility between the fluorine resins having a difference in the cohesive energy.

Therefore, the fluorine resin combined with the main fluorine resin may be, but not limited thereto, a resin which 1) has a close melting point, 2) is not compatible, and 3) has a difference between the length of the C—F bonds or the C—H bonds in the molecule or a difference in cohesive energy in the relationship with the main fluorine resin. For example, the combination of the fluorine resin combined with the main fluorine resin includes a combination of a tetrafluoroethylene-hexafluoropropylene-perfluoroalkyl vinyl ether copolymer and a tetrafluoroethylene-ethylene copolymer, a combination of the THV and a polyvinylidene fluoride (PVDF), but not limited thereto. As for the resin combined with the main fluorine resin, any resin other than the fluorine resin may be available, as long as the resin 1) has a close melting point and 2) is incompatible. However, a fluorine resin, which has a similar basic structure to that of the main fluorine resin and may be different in terms of the cohesive energy, is more preferable.

An aspect of the present invention includes a heat-shrinkable tube having tearability which contains a tetrafluoroethylene-hexafluoropropylene-perfluoroalkyl vinyl ether copolymer and a tetrafluoroethylene-ethylene copolymer, and another aspect includes a heat-shrinkable tube having tearability which contains THV and PVDF.

Further, by setting the mixing ratio of the main fluorine resin (e.g., a tetrafluoroethylene-hexafluoropropylene-perfluoroalkyl vinyl ether copolymer) and the fluorine resin other than the main fluorine resin (e.g., a tetrafluoroethylene-ethylene copolymer) to a range from 98:2 to 70:30 by mass ratio, the heat-shrinkable tube having tearability made of the fluorine resin which has significantly excellent heat-shrinkability and tearability may be obtained. Furthermore, the mixing ratio of the main fluorine resin (e.g., a tetrafluoroethylene-hexafluoropropylene-perfluoroalkyl vinyl ether copolymer) and the fluorine resin other than the main fluorine resin (e.g., a tetrafluoroethylene-ethylene copolymer) is more preferably from 98:2 to 80:20, and still more preferably from 95:5 to 80:20.

As for the heat-shrinkable tube having tearability made of the fluorine resin of the present invention, it is possible to, after the raw materials are blended, perform the tube forming by a sizing plate method using a single-screw melt extruder having a cylinder diameter of 20 mm at a screw rotation speed of 10 rpm.

The temperature conditions may be set to a die temperature of 360° C. to 400° C.

Further, it is possible to increase the stability during molding by changing the temperature in consideration of the molding conditions depending on the mixing ratio of the resins.

Then, it is possible to impart the heat-shrinkability by filling pressurized nitrogen inside the shaped tube made of the fluorine resin so as to expand the tube. The pressure of the gas supplied inside the tube made of the fluorine resin when the tube is expanded may be applied by supplying the pressure in the range in which each of the tube made of a fluorine resin is not destroyed.

Hereinafter, the present invention will be described as shown in Examples and Comparative Examples.

EXAMPLES (1) Loss Energy, Elastic Modulus, and Tan δ

The viscoelastic data was obtained by a DMA (dynamic viscoelasticity) measurement using a thermal mechanical analyzer, TMA4000, manufactured by Bruker AXS, Inc.

Figure 1:
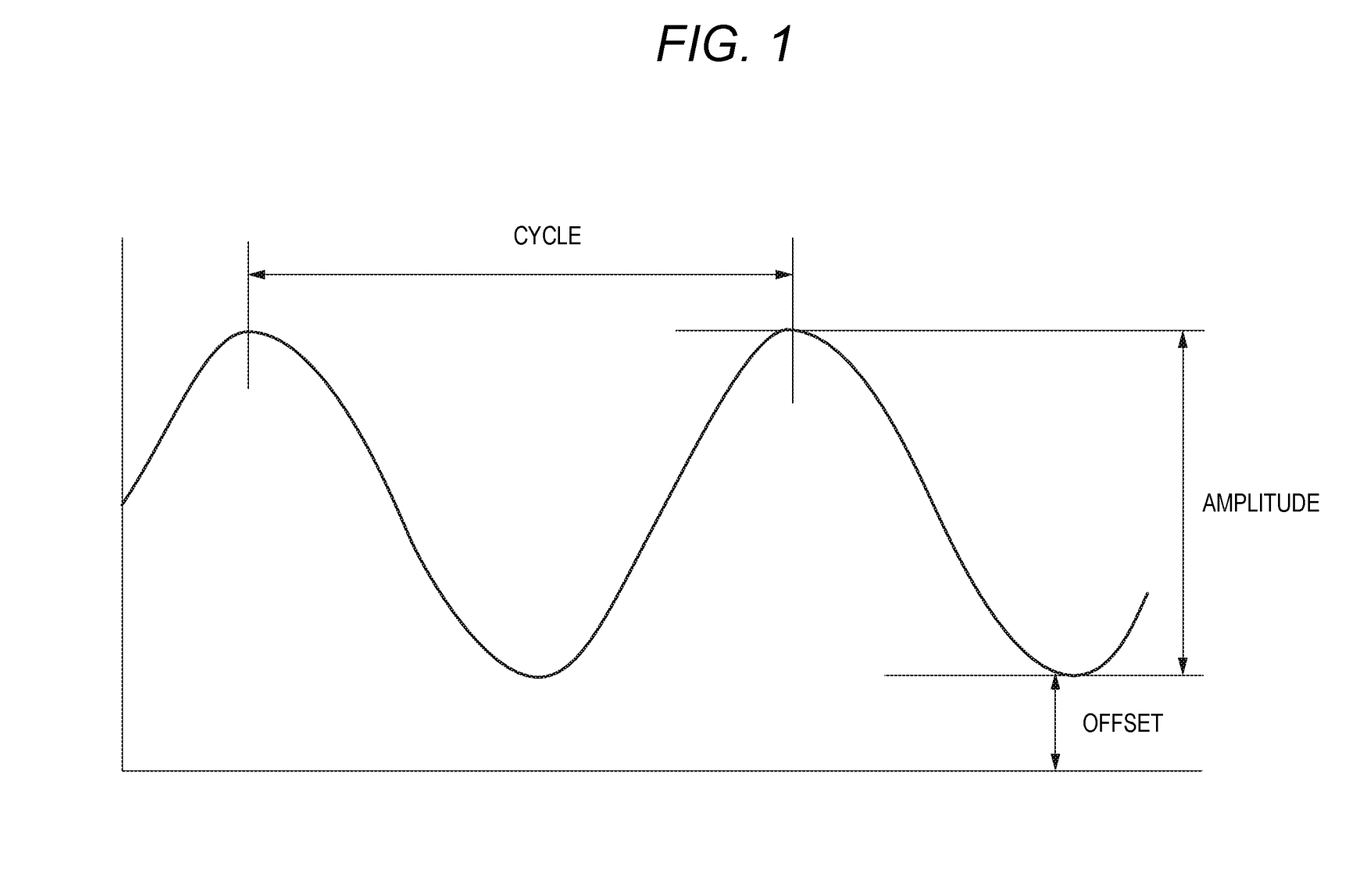
FIG. 1 is a diagram related to DMA measurements according to the present invention for illustrating a sinusoidal wave stress.
Figure 2:
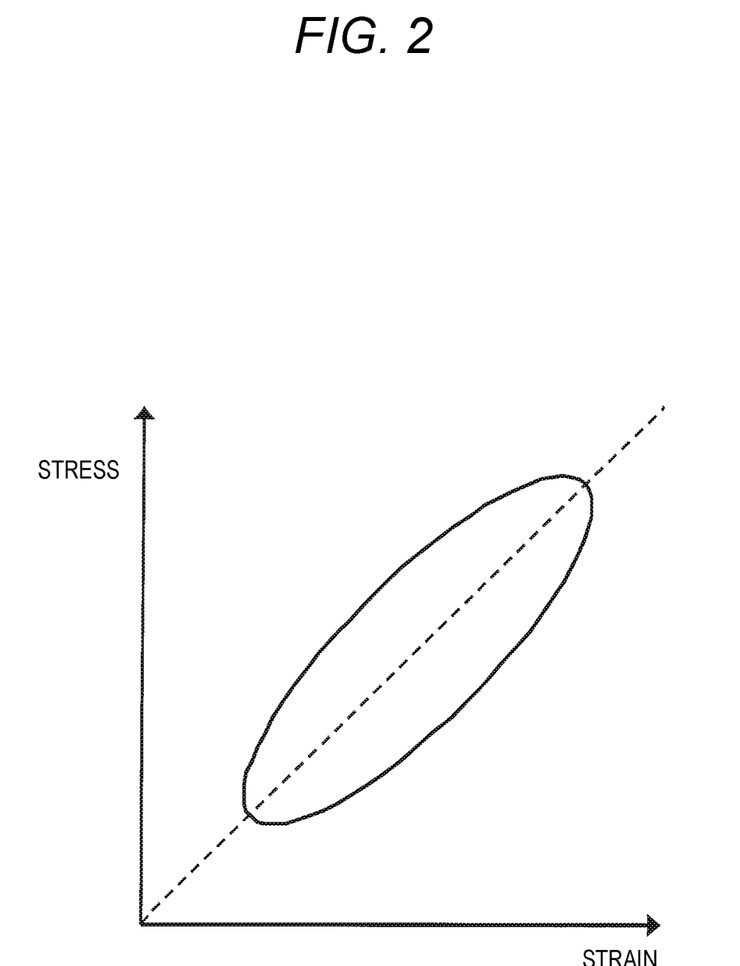
FIG. 2 is a diagram representing a relationship between stress and strain when the sinusoidal wave stress is applied to a sample.

<Measurement Sample>
Fabrication method: a measurement sample was obtained by melt pressing a test tube with a thermal press manufactured by Toho Machinery Co., Ltd. which was set to a temperature of 310° C. (however, 260° C. in Example 3) and a pressure of 200 to 400 N/cm$^2$, and then by immediately water-cooling the tube with a water-cooled press.
Size (length×width×thickness): 20 mm×5 mm×200 to 400 μm
<Fixation of Sample>
Distance between the chucks: 15 mm.
<Temperature Program>
Rate of temperature increase: 5° C./min.
<Loading Program>
Loading mode: loading cycle of a sine wave (periodic stress)
Offset value: −3 g
Amplitude: 10 g (−3 to −13 g)
Cycle: 30 sec
* See FIG. 1.
<Analysis Method>
If the data of the stress and the strain when a sine wave stress was applied to the sample is represented in a stress-strain coordinates for one cycle, an ellipse is drawn as illustrated in FIG. 2.

Here, the slope of the ellipse represents an elastic modulus, and the area of the ellipse represents a loss energy. The tan δ is obtained by a phase difference between the stress data and the strain data.

In the accessory analysis software, the calculation of the viscoelastic data for each cycle is performed by dividing the data per one cycle automatically from the measured data.

(2) Glass Transition Temperature

From the tan δ chart by the above-mentioned DMA measurement, the temperature corresponding to the peak was determined as the glass transition temperature.

Example 1

Preparation of Sample

Mixtures of a tetrafluoroethylene-hexafluoropropylene-perfluoroalkyl vinyl ether copolymer (FEP-130J produced by Du Pont-Mitsui Fluorochemicals Co., Ltd., Tg of 72° C.) and a tetrafluoroethylene-ethylene copolymer (FIFE: C-55AP produced by Asahi Glass Co., Ltd.) were prepared by varying their mixing ratio. Each mixture was shaped into pellets by using a biaxial extruder having a cylinder diameter of 20 mm, at a screw rotation speed of 45 rpm and at the die temperature of 320° C. The pellets were used and tube forming was performed by a sizing plate method using a single screw extruder having a cylinder diameter of 20 mm at a screw rotation speed of 10 rpm and at the die temperature of 390° C. As a result, samples having an inner diameter of 0.5 mm, an outer diameter of 0.9 mm, and a thickness of 0.2 mm were produced.

(Test of Tear Strength)
After checking whether the samples were torn by hands without using instruments, as for samples that could not be torn by hand only, the incision was made with a razor and then Whether the tearing from the incision portion is possible was tested. As for the sample in which the tearing was possible, an incision of 40 mm was formed at one end of the sample having a length of 100 mm, and the sample was torn at a rate of 200 mm/min by a tensile tester. The maximum force at that time was measured as tear strength.

Further, the length which could be torn without breaking when the sample was torn was measured as the tear straightness. Furthermore, the measurement was performed three times on the samples of the same composition to obtain a weighted average value. The results are shown in Table 1.

TABLE 1

| Sample No. | ETFE ratio (% by mass) | Tearability | Tear Straightness (mm) | Tear Strength (N) |
|---|---|---|---|---|
| 1-1 | 5 | Incision is needed | ~20 | 2.9 |
| 1-2 | 7 | Incision is needed | ~900 | 2.7 |
| 1-3 | 10 | Incision is needed | 1000 or more | 2.4 |
| 1-4 | 20 | Incision is needed | 1000 or more | 1.7 |
| 1-5 | 30 | Incision is needed | 1000 or more | 0.7 |
| 1-6 | 40 | Torn by only hands | 1000 or more | 0.3 |

(Test of Expansion and Heat-Shrinkability)

The test tubes were prepared by changing the mixing ratio of raw materials, and mounted on the expansion test apparatus, and the pressurized nitrogen was injected inside the tubes to measure whether the tubes are expandable without breakdown. The results are shown in the following table.

As for the mixture of a tetrafluoroethylene-hexafluoropropylene-perfluoroalkyl vinyl ether copolymer (FEP-130J produced by Du Pont-Mitsui Fluorochemicals Co., Ltd.) and a tetrafluoroethylene-ethylene copolymer (ETFE: C-55AP produced by Asahi Glass Co., Ltd.) used in the test, if the tetrafluoroethylene-ethylene copolymer was not less than 5% by mass of the total, it was confirmed that the tearability and the heat-shrinkability could be obtained.

Then, five samples in which the tetrafluoroethylene-ethylene copolymer (ETFE) was contained by 5% by mass, 7% by mass, 10% by mass, 20% by mass, and 30% by mass of the total, respectively, were prepared, the pressurized nitrogen was applied to each sample, the samples were expanded as large as possible so as not to be destroyed, and then their sizes were measured. Subsequently, each sample was heat-shrunk by heating the sample under the conditions of 200° C. and 20 min, and the size after its heat shrink was measured in the same manner. As for Samples 2-1 to 2-5 in which the concentration of the ETFE is 5% by mass, the results are shown in Table 2. Further, as for Samples 3-1 to 3-5 in which the concentration of the ETFE is 7% by mass, the results are shown in Table 3. In addition, as for Samples 4-1 to 4-5 in which the concentration of the ETFE is 10% by mass, the results are shown in Table 4. Further, as for Samples 5-1 to 5-5 in which the concentration of the ETFE is 20% by mass, the results are shown in Table 5. Moreover, as for Samples 6-1 to 6-5 in which the concentration of the ETFE is 30% by mass, the results are shown in Table 6.

Meanwhile, as for the samples in which the concentration of the ETFE is 40% by mass and 30% by mass, the resin is easily liberized by pellet forming and thus the pelletization is difficult to be performed. As far in terms of productivity, the upper limit is considered to be up to about 20% by mass for stable manufacturing range.

TABLE 2

| | Before Heat Shrink | | | After Heat Shrink | | | Change Rate (%) | | |
|---|---|---|---|---|---|---|---|---|---|
| | Inner Diameter | Outer Diameter | Length | Inner Diameter | Outer Diameter | Length | Inner Diameter | Outer Diameter | Length |
| 2-1 | 1.02 | 1.32 | 100.0 | 0.58 | 0.97 | 117.0 | 43.14 | 26.52 | −17.00 |
| 2-2 | 1.05 | 1.33 | 100.0 | 0.57 | 0.97 | 117.0 | 45.71 | 27.07 | −17.00 |
| 2-3 | 1.07 | 1.35 | 100.0 | 0.56 | 0.97 | 117.0 | 47.66 | 28.15 | −17.00 |
| 2-4 | 1.12 | 1.39 | 100.0 | 0.56 | 0.97 | 117.0 | 50.00 | 30.22 | −17.00 |
| 2-5 | 1.14 | 1.42 | 100.0 | 0.56 | 0.98 | 116.0 | 50.88 | 30.99 | −16.00 |
| Average | 1.08 | 1.36 | 100.0 | 0.57 | 0.97 | 116.8 | 47.48 | 28.59 | −16.80 |

TABLE 3

| | Before Heat Shrink | | | After Heat Shrink | | | Change Rate (%) | | |
|---|---|---|---|---|---|---|---|---|---|
| | Inner Diameter | Outer Diameter | Length | Inner Diameter | Outer Diameter | Length | Inner Diameter | Outer Diameter | Length |
| 3-1 | 1.08 | 1.35 | 100.0 | 0.57 | 0.96 | 116.0 | 47.22 | 28.89 | −16.50 |
| 3-2 | 1.08 | 1.37 | 100.0 | 0.57 | 0.97 | 116.5 | 47.22 | 29.20 | −16.50 |
| 3-3 | 1.09 | 1.36 | 100.0 | 0.57 | 0.97 | 116.0 | 47.71 | 28.68 | −16.00 |
| 3-4 | 1.10 | 1.39 | 100.0 | 0.57 | 0.97 | 116.0 | 48.18 | 30.22 | −16.00 |
| 3-5 | 1.12 | 1.39 | 100.0 | 0.57 | 0.97 | 116.5 | 49.11 | 30.22 | −16.50 |
| Average | 1.09 | 1.37 | 100.0 | 0.57 | 0.97 | 116.2 | 47.89 | 29.44 | −16.20 |

TABLE 4

| | Before Heat Shrink | | | After Heat Shrink | | | Change Rate (%) | | |
|---|---|---|---|---|---|---|---|---|---|
| | Inner Diameter | Outer Diameter | Length | Inner Diameter | Outer Diameter | Length | Inner Diameter | Outer Diameter | Length |
| 4-1 | 1.05 | 1.32 | 100.0 | 0.58 | 0.97 | 115.0 | 44.76 | 26.52 | −15.00 |
| 4-2 | 1.06 | 1.34 | 100.0 | 0.57 | 0.97 | 115.5 | 46.23 | 27.61 | −15.50 |
| 4-3 | 1.07 | 1.34 | 100.0 | 0.57 | 0.97 | 115.0 | 46.73 | 27.61 | −15.00 |
| 4-4 | 1.07 | 1.33 | 100.0 | 0.57 | 0.97 | 115.0 | 46.73 | 27.07 | −15.00 |
| 4-5 | 1.12 | 1.38 | 100.0 | 0.57 | 0.97 | 115.5 | 49.11 | 29.71 | −15.50 |
| Average | 1.07 | 1.34 | 100.0 | 0.57 | 0.97 | 115.3 | 46.71 | 27.70 | −15.30 |

TABLE 5

| | Before Heat Shrink | | | After Heat Shrink | | | Change Rate (%) | | |
|---|---|---|---|---|---|---|---|---|---|
| | Inner Diameter | Outer Diameter | Length | Inner Diameter | Outer Diameter | Length | Inner Diameter | Outer Diameter | Length |
| 5-1 | 0.99 | 1.30 | 100.0 | 0.56 | 0.96 | 115.0 | 43.43 | 26.15 | −15.00 |
| 5-2 | 0.99 | 1.29 | 100.0 | 0.56 | 0.96 | 115.0 | 43.43 | 25.58 | −15.00 |
| 5-3 | 0.99 | 1.30 | 100.0 | 0.56 | 0.96 | 115.0 | 43.43 | 26.15 | −15.00 |
| 5-4 | 0.98 | 1.28 | 100.0 | 0.56 | 0.96 | 115.0 | 42.86 | 25.00 | −15.00 |
| 5-5 | 0.99 | 1.29 | 100.0 | 0.56 | 0.96 | 115.0 | 43.43 | 25.58 | −15.00 |
| Average | 0.99 | 1.29 | 100.0 | 0.56 | 0.96 | 115.0 | 43.32 | 25.69 | −15.00 |

TABLE 6

| | Before Heat Shrink | | | After Heat Shrink | | | Change Rate (%) | | |
|---|---|---|---|---|---|---|---|---|---|
| | Inner Diameter | Outer Diameter | Length | Inner Diameter | Outer Diameter | Length | Inner Diameter | Outer Diameter | Length |
| 6-1 | 0.66 | 1.03 | 100.0 | 0.53 | 0.95 | 103.0 | 19.70 | 7.77 | −3.00 |
| 6-2 | 0.67 | 1.04 | 100.0 | 0.54 | 0.95 | 103.0 | 19.40 | 8.65 | −3.00 |
| 6-3 | 0.68 | 1.04 | 100.0 | 0.53 | 0.95 | 103.0 | 22.06 | 8.65 | −3.00 |
| 6-4 | 0.68 | 1.04 | 100.0 | 0.53 | 0.94 | 103.0 | 22.06 | 9.62 | −3.00 |
| 6-5 | 0.68 | 1.04 | 100.0 | 0.53 | 0.94 | 102.5 | 22.06 | 9.62 | −2.50 |
| Average | 0.67 | 1.04 | 100.0 | 0.53 | 0.95 | 102.9 | 21.06 | 8.86 | −2.90 |

Example 2

Preparation of Sample

Mixtures of a tetrafluoroethylene-hexafluoropropylene-perfluoroalkyl vinyl ether copolymer (FEP-NP120 produced by Daikin Industries, Ltd., Tg of 74° C.) and a tetrafluoroethylene-ethylene copolymer (ETFE: C-55AP produced by Asahi Glass Co., Ltd.) were prepared by varying their mixing ratio. Each mixture was used and shaped into pellets by using a biaxial extruder having a cylinder diameter of 20 mm, at a screw rotation speed of 45 rpm and at the die temperature of 320° C.

Next, the obtained pellets were used and tube forming was performed by a sizing plate method using a single screw extruder having a cylinder diameter of 20 mm at a screw rotation speed of 10 rpm and at the die temperature of 390° C. As a result, Samples 7-1 to 7-4 having an inner diameter of 0.5 mm, an outer diameter of 0.9 mm, and a thickness of 0.2 mm were produced.

(Test of Tear Strength)

After checking whether the tearing from the incision portion is possible or not by putting the incision with a razor, as for the sample in which the tearing was possible, an incision of 40 mm was formed at one end of the sample having a length of 100 mm, and the sample was torn at a rate of 200 mm/min by a tensile tester. The maximum force at that time was measured as tear strength. Further, the measurement was performed three times on the samples of the same composition to obtain a weighted average value. The results are shown in Table 7. Furthermore, the length of samples which could be torn without breaking was shown in Table 7 as the tear straightness when the samples having incisions put with a razor were torn.

TABLE 7

| Sample No. | ETFE ratio (% by mass) | Tearability | Tear Straightness (mm) | Tear Strength (N) |
|---|---|---|---|---|
| 7-1 | 2 | Incision is needed | ~50 | 3.19 |
| 7-2 | 5 | Incision is needed | ~400 | 2.92 |
| 7-3 | 7 | Incision is needed | ~900 | 2.67 |
| 7-4 | 10 | Incision is needed | 1000 or more | 2.34 |

(Test of Expansion and Heat-Shrinkability)

The test tubes were prepared by changing the mixing ratio of raw materials, and mounted on the expansion test apparatus, and the pressurized nitrogen was injected inside the tubes to measure whether the tubes are expandable without breakdown. The results are shown in the following table.

As for the prepared mixture of a tetrafluoroethylene-ethylene copolymer (ETFE: C-55AP produced by Asahi Glass Co., Ltd.) and a tetrafluoroethylene-hexafluoropropylene-perfluoroalkyl vinyl ether copolymer (FEP-NP120 produced by Daikin Industries, Ltd.), if the tetrafluoroethylene-ethylene copolymer was not less than 2% by mass of the total, it was confirmed that the tearability and the heat-shrinkability could be obtained.

Then, five samples in which the tetrafluoroethylene-ethylene copolymer (ETFE) was 2% by mass, 5% by mass, 7% by mass, and 10% by mass of the total, respectively, were prepared, the pressurized nitrogen was applied to each sample, the samples were expanded as large as possible so as not to be destroyed, and then their sizes were measured. Subsequently, each sample was heat-shrunk by heating the sample under the conditions of 200° C. and 20 min, and the size after its heat shrink was also measured in the same manner.

As for Samples 8-1 to 8-5 in which the concentration of the ETFE is 2% by mass, the results are shown in Table 8. As for Samples 9-1 to 9-5 in which the concentration of the ETFE is 5% by mass, the results are shown in Table 9. As for Samples 10-1 to 10-5 in which the concentration of the ETFE is 7% by mass, the results are shown in Table 10. Further, as for Samples 11-1 to 11-5 in which the concentration of the ETFE is 10% by mass, the results are shown in Table 11.

TABLE 8

| | Before Heat Shrink | | | After Heat Shrink | | | Change Rate (%) | | |
|---|---|---|---|---|---|---|---|---|---|
| | Inner Diameter | Outer Diameter | Length | Inner Diameter | Outer Diameter | Length | Inner Diameter | Outer Diameter | Length |
| 8-1 | 1.01 | 1.32 | 100.0 | 0.56 | 0.96 | 116.5 | 44.55 | 27.27 | −16.50 |
| 8-2 | 1.01 | 1.30 | 100.0 | 0.56 | 0.96 | 116.0 | 44.55 | 26.15 | −16.00 |
| 8-3 | 1.04 | 1.33 | 100.0 | 0.57 | 0.96 | 116.0 | 45.19 | 27.82 | −16.00 |
| 8-4 | 1.02 | 1.31 | 100.0 | 0.56 | 0.96 | 116.5 | 45.10 | 26.72 | −16.50 |
| 8-5 | 1.04 | 1.32 | 100.0 | 0.57 | 0.96 | 116.0 | 45.19 | 27.27 | −16.00 |
| Average | 1.02 | 1.32 | 100.0 | 0.56 | 0.96 | 116.2 | 44.92 | 27.05 | −16.20 |

TABLE 9

| | Before Heat Shrink | | | After Heat Shrink | | | Change Rate (%) | | |
|---|---|---|---|---|---|---|---|---|---|
| | Inner Diameter | Outer Diameter | Length | Inner Diameter | Outer Diameter | Length | Inner Diameter | Outer Diameter | Length |
| 9-1 | 1.03 | 1.32 | 100.0 | 0.57 | 0.96 | 115.5 | 44.66 | 27.27 | −15.50 |
| 9-2 | 1.05 | 1.33 | 100.0 | 0.57 | 0.96 | 115.0 | 45.71 | 27.82 | −15.00 |
| 9-3 | 1.05 | 1.34 | 100.0 | 0.57 | 0.96 | 115.5 | 45.71 | 28.36 | −15.50 |
| 9-4 | 1.05 | 1.33 | 100.0 | 0.57 | 0.97 | 115.0 | 45.71 | 27.07 | −15.00 |
| 9-5 | 1.06 | 1.35 | 100.0 | 0.57 | 0.96 | 115.0 | 46.23 | 28.89 | −15.00 |
| Average | 1.05 | 1.33 | 100.0 | 0.57 | 0.96 | 115.2 | 45.61 | 27.88 | −15.20 |

TABLE 10

| | Before Heat Shrink | | | After Heat Shrink | | | Change Rate (%) | | |
|---|---|---|---|---|---|---|---|---|---|
| | Inner Diameter | Outer Diameter | Length | Inner Diameter | Outer Diameter | Length | Inner Diameter | Outer Diameter | Length |
| 10-1 | 0.96 | 1.28 | 100.0 | 0.56 | 0.95 | 113.5 | 41.67 | 25.78 | −13.50 |
| 10-2 | 0.98 | 1.26 | 100.0 | 0.56 | 0.95 | 115.0 | 42.86 | 24.60 | −15.00 |
| 10-3 | 0.99 | 1.27 | 100.0 | 0.56 | 0.95 | 115.0 | 43.43 | 25.20 | −15.00 |
| 10-4 | 0.99 | 1.27 | 100.0 | 0.55 | 0.95 | 113.5 | 44.44 | 25.20 | −13.50 |
| 10-5 | 0.99 | 1.28 | 100.0 | 0.55 | 0.95 | 114.5 | 44.44 | 25.78 | −14.50 |
| Average | 0.98 | 1.27 | 100.0 | 0.56 | 0.95 | 114.3 | 43.37 | 25.31 | −14.30 |

TABLE 11

| | Before Heat Shrink | | | After Heat Shrink | | | Change Rate (%) | | |
|---|---|---|---|---|---|---|---|---|---|
| | Inner Diameter | Outer Diameter | Length | Inner Diameter | Outer Diameter | Length | Inner Diameter | Outer Diameter | Length |
| 11-1 | 0.93 | 1.23 | 100.0 | 0.55 | 0.95 | 113.5 | 40.86 | 22.76 | −13.50 |
| 11-2 | 0.93 | 1.23 | 100.0 | 0.55 | 0.95 | 113.0 | 40.86 | 22.76 | −13.00 |
| 11-3 | 0.93 | 1.22 | 100.0 | 0.55 | 0.95 | 113.0 | 40.86 | 22.13 | −13.00 |
| 11-4 | 0.93 | 1.22 | 100.0 | 0.56 | 0.95 | 113.0 | 39.78 | 22.13 | −13.00 |
| 11-5 | 0.93 | 1.22 | 100.0 | 0.55 | 0.95 | 113.0 | 40.86 | 22.76 | −13.00 |
| Average | 0.93 | 1.23 | 100.0 | 0.55 | 0.95 | 113.1 | 40.65 | 22.51 | −13.10 |

Comparative Example 1

Preparation of Sample

Mixtures of a tetrafluoroethylene-hexafluoropropylene copolymer (FEP-100 J produced by Du Pont-Mitsui Fluorochemicals Co., Ltd.) and a tetrafluoroethylene-ethylene copolymer (ETFE: C-88AX produced by Asahi Glass Co., Ltd.) were prepared by varying their mixing ratio. Each mixture was used and tube forming was performed by a sizing plate method using a single screw extruder having a cylinder diameter of 20 mm at a screw rotation speed of 10 rpm and at the die temperature of 390° C. As a result, samples having an inner diameter of 1.0 mm, an outer diameter of 1.4 mm, and a thickness of 0.2 mm were produced.

(Test of Tear Strength)

After checking whether the tearing is possible or not only by hands without using instruments or whether the tearing from the incision portion is possible or not by putting an incision with a razor, as for the things in which the tearing was possible, an incision of 40 mm was formed at one end of the sample having a length of 100 mm, and the sample was torn at a rate of 200 mm/min by a tensile tester. The maximum force at that time was measured as tear strength. Further, the measurement was performed three times on the samples of the same composition to obtain a weighted average value. The results are shown in Table 12.

TABLE 12

| Sample No. | ETFE ratio (% by mass) | Tearability | Tear Strength (N) |
|---|---|---|---|
| 12-1 | 1 | Tearing is not possible | — |
| 12-2 | 2 | Tearing is not possible | — |
| 12-3 | 3 | Incision is needed | 3.89 |
| 12-4 | 5 | Incision is needed | 4.00 |
| 12-5 | 10 | Incision is needed | 3.26 |
| 12-6 | 20 | Incision is needed | 1.81 |
| 12-7 | 30 | Torn by hands | 0.36 |
| 12-8 | 40 | Torn by hands | 0.43 |
| 12-9 | 50 | Torn by hands | 0.74 |
| 12-10 | 60 | Tearing is not possible | — |

(Test of Expansion and Heat-Shrinkability)

The pressurized nitrogen was injected inside the shaped tubes by expansion means to determine whether the tubes are expandable without breakdown. As for the mixture of a tetrafluoroethylene-ethylene copolymer (ETFE: C-88AX produced by Asahi Glass Co., Ltd.) and a tetrafluoroethylene-hexafluoropropylene copolymer (FEP-100J produced by Du. Pont-Mitsui Fluorochemicals Co., Ltd.) used in the test, if the tetrafluoroethylene-ethylene copolymer took from 3% by mass to 10% by mass of the total, it was confirmed that the tearability and the heat-shrinkability could be obtained.

Then, five samples in which a tetrafluoroethylene-ethylene copolymer (ETFE) was 10% by mass of the total were prepared, the pressurized nitrogen was applied to each sample, the samples were expanded as large as possible so as not to be destroyed, and then their sizes Were measured. Subsequently, each sample was heat-shrunk by heating the sample under the conditions of 200° C. and 20 min, and the size after its heat shrink was also measured in the same manner. As for Samples 13-1 to 13-5 in which the concentration of the ETFE is 10% by mass, the results are shown in Table 13.

TABLE 13

| | Before Heat Shrink | | | After Heat Shrink | | | Change Rate (%) | | |
|---|---|---|---|---|---|---|---|---|---|
| | Inner Diameter | Outer Diameter | Length | Inner Diameter | Outer Diameter | Length | Inner Diameter | Outer Diameter | Length |
| 13-1 | 1.09 | 1.45 | 150.0 | 1.00 | 1.40 | 151.0 | 8.26 | 3.45 | −0.67 |
| 13-2 | 1.09 | 1.45 | 150.0 | 1.00 | 1.39 | 151.0 | 8.26 | 4.14 | −0.67 |
| 13-3 | 1.11 | 1.46 | 150.0 | 1.00 | 1.40 | 151.0 | 9.91 | 4.11 | −0.67 |
| 13-4 | 1.11 | 1.46 | 150.0 | 1.00 | 1.40 | 151.0 | 9.91 | 4.11 | −0.67 |
| 13-5 | 1.11 | 1.47 | 150.0 | 1.00 | 1.40 | 151.0 | 9.91 | 4.76 | −0.67 |
| Average | 1.102 | 1.458 | 150.0 | 1.00 | 1.40 | 151.0 | 9.25 | 4.11 | −0.67 |

Example 3

Preparation of Sample

Mixtures of a terpolymer (THV: Tg of 46° C.) of about 10 mol % of vinylidene fluoride, about 70 mol % of tetrafluoroethylene and about 20 mol % of hexafluoropropylene, and a polyvinylidene fluoride (PVDF: KYNAR 740 produced by ARKEMA (Arkema)) was prepared by varying their mixing ratio. Each mixture was used and shaped into pellets by using a biaxial extruder having a cylinder diameter of 20 mm, at a screw rotation speed of 45 rpm and at the die temperature of 280° C.

Next, the obtained pellets were used and tube forming was performed by a sizing plate method using a single screw extruder having a cylinder diameter of 20 mm at a screw rotation speed of 10 rpm and at the die temperature of 340° C. As a result, samples of 14-1 to 14-3 having an inner diameter of 0.5 mm, an outer diameter of 0.9 mm, and a thickness of 0.2 mm were produced.

(Test of Tear Strength)

After checking whether the tearing from the incision portion is possible or not by putting the incision with a razor, as for the sample in which the tearing was possible, the incision of 40 mm was formed at one end of the sample having a length of 100 mm, and the sample was torn at a rate of 200 mm/min by a tensile tester. The maximum force at that time was measured as tear strength. Further, the measurement was performed three times on the samples of the same composition to obtain a weighted average value. The results are shown in Table 14.

TABLE 14

| Sample No. | PVDF ratio (% by mass) | Tearability | Tear Strength (N) |
|---|---|---|---|
| 14-1 | 2 | Incision is needed | 3.2 |
| 14-2 | 20 | Incision is needed | 1.9 |
| 14-3 | 30 | Incision is needed | 1.0 |

(Test of Expansion and Heat-Shrinkability)

The test tubes were prepared by changing the mixing ratio of raw materials, and mounted on the expansion test apparatus, and the pressurized nitrogen was injected inside the tubes to determine whether the tubes are expandable without breakdown. The results are shown in the following table. As for the mixture of a polyvinylidene fluoride (PVDF: KYNAR 740 produced by ARKEMA (Arkema)) and the THV produced in this example, if the polyvinylidene fluoride was not less than 2% by mass of the total, it was confirmed that the tearability and the heat-shrinkability could be obtained.

Then, samples in which polyvinylidene fluoride (PVDF) was 2% by mass, 20% by mass, and 30% by mass of the total, respectively, was prepared, the pressurized nitrogen was applied to each sample, the samples were expanded as large as possible so as not to be destroyed, and then their sizes were measured. Subsequently, each sample was heat-shrunk by heating the sample under the conditions of 200° C., and 20 min, and the size after its heat shrink was also measured in the same manner.

As for Sample 15-1 in which the concentration of the PVDF is 2% by mass, the results are shown in Table 15. As for Sample 16-1 in which the concentration of the PVDF is 20% by mass, the results are shown in Table 16. As for Sample of 17-1 in which the concentration of the PVDF is 30% by mass, the results are shown in Table 17.

TABLE 15

| | Inner Diameter Before Heat Shrink | Inner Diameter After Heat Shrink | Change Rate (%) |
|---|---|---|---|
| 15-1 | 1.20 | 0.51 | 57.3 |

TABLE 16

| | Inner Diameter Before Heat Shrink | Inner Diameter After Heat Shrink | Change Rate (%) |
|---|---|---|---|
| 16-1 | 1.19 | 0.53 | 55.5 |

TABLE 17

| | Inner Diameter Before Heat Shrink | Inner Diameter After Heat Shrink | Change Rate (%) |
|---|---|---|---|
| 17-1 | 1.19 | 0.55 | 53.8 |

The data of the characteristics for each sample are shown, in Table 18.

TABLE 18

Figure 3:
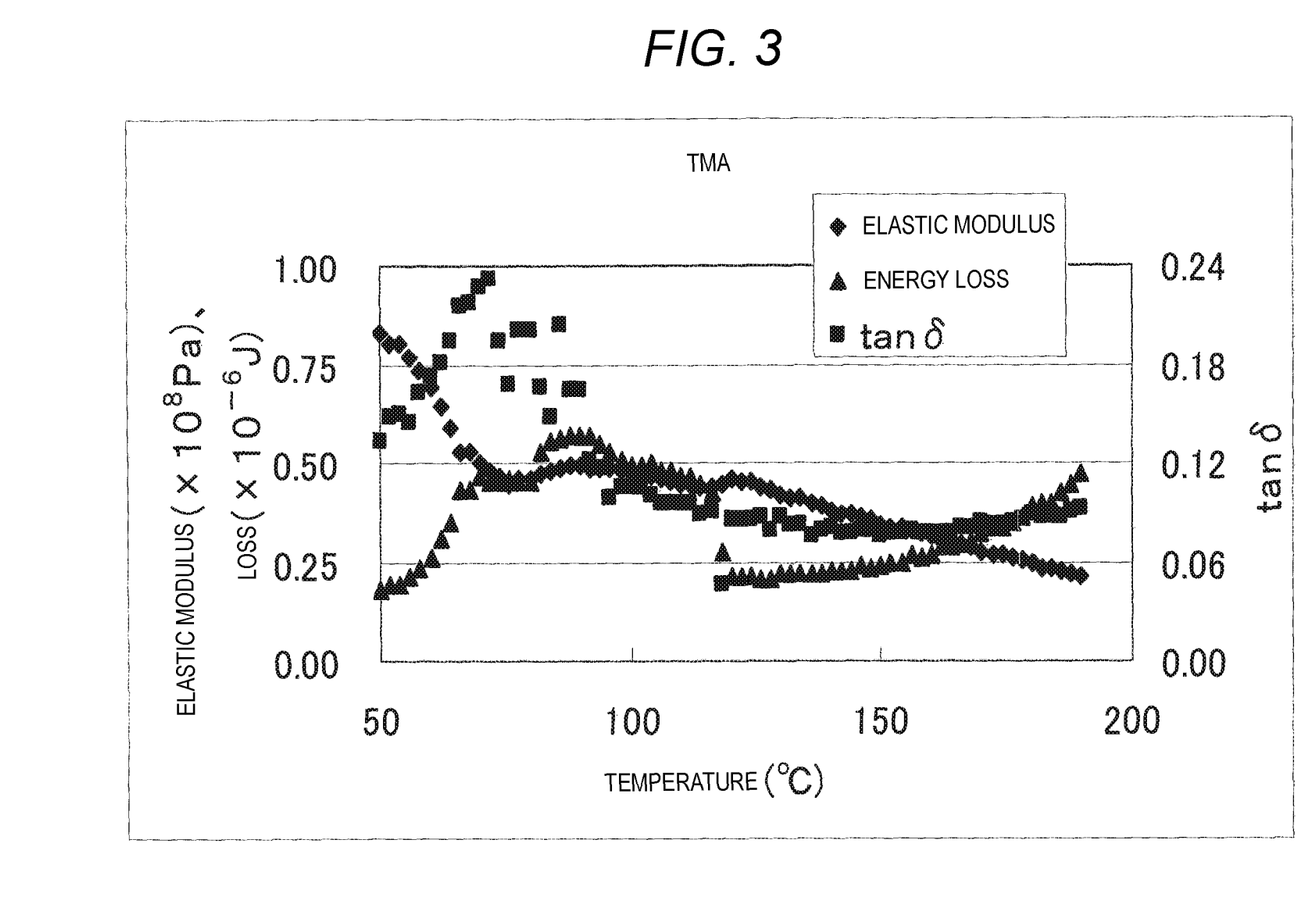
FIG. 3 is a graph showing a viscoelasticity of the tube of Example 1.
Figure 4:
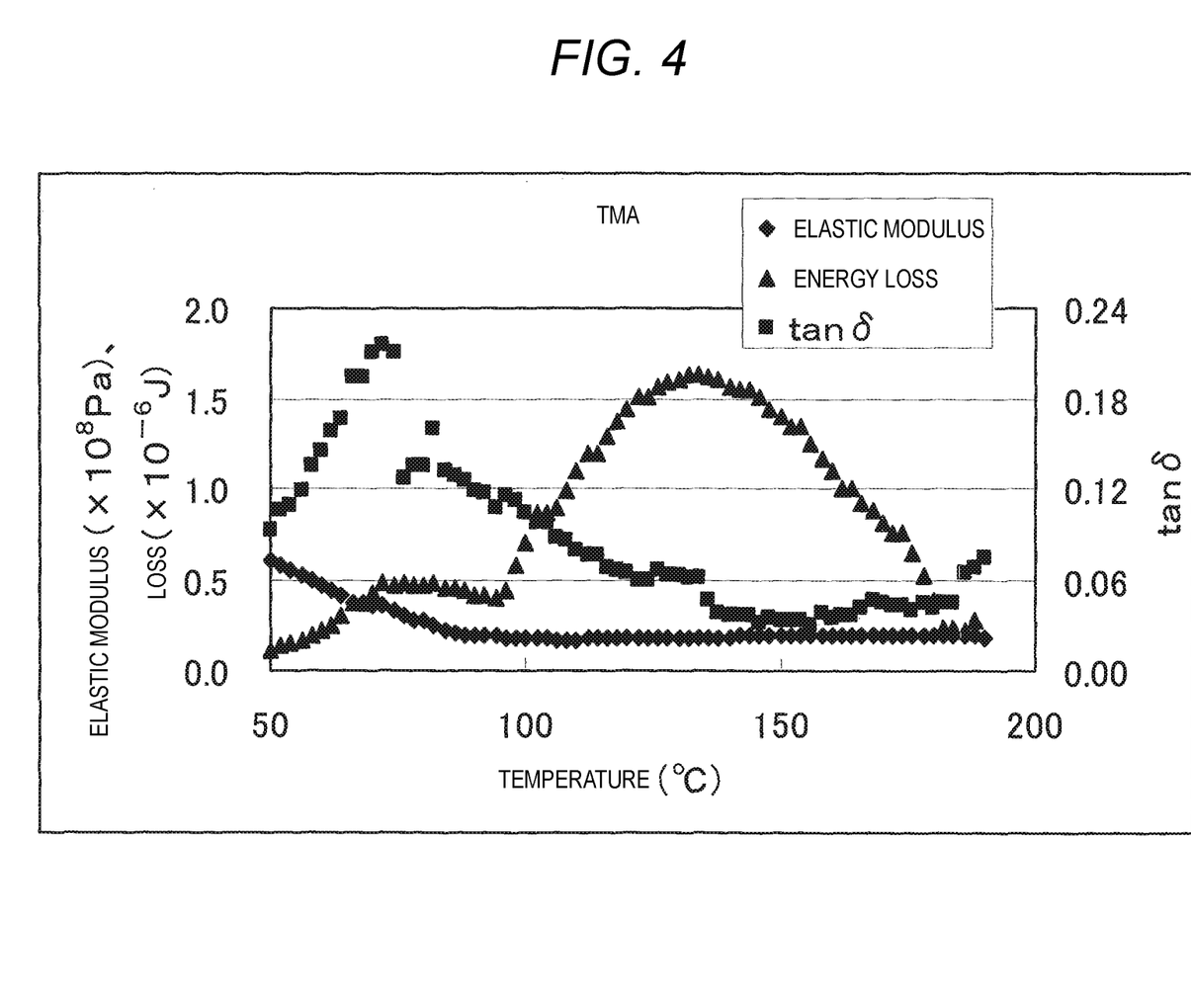
FIG. 4 is a graph showing a viscoelasticity of the tube of Comparative Example 1.
Figure 5:
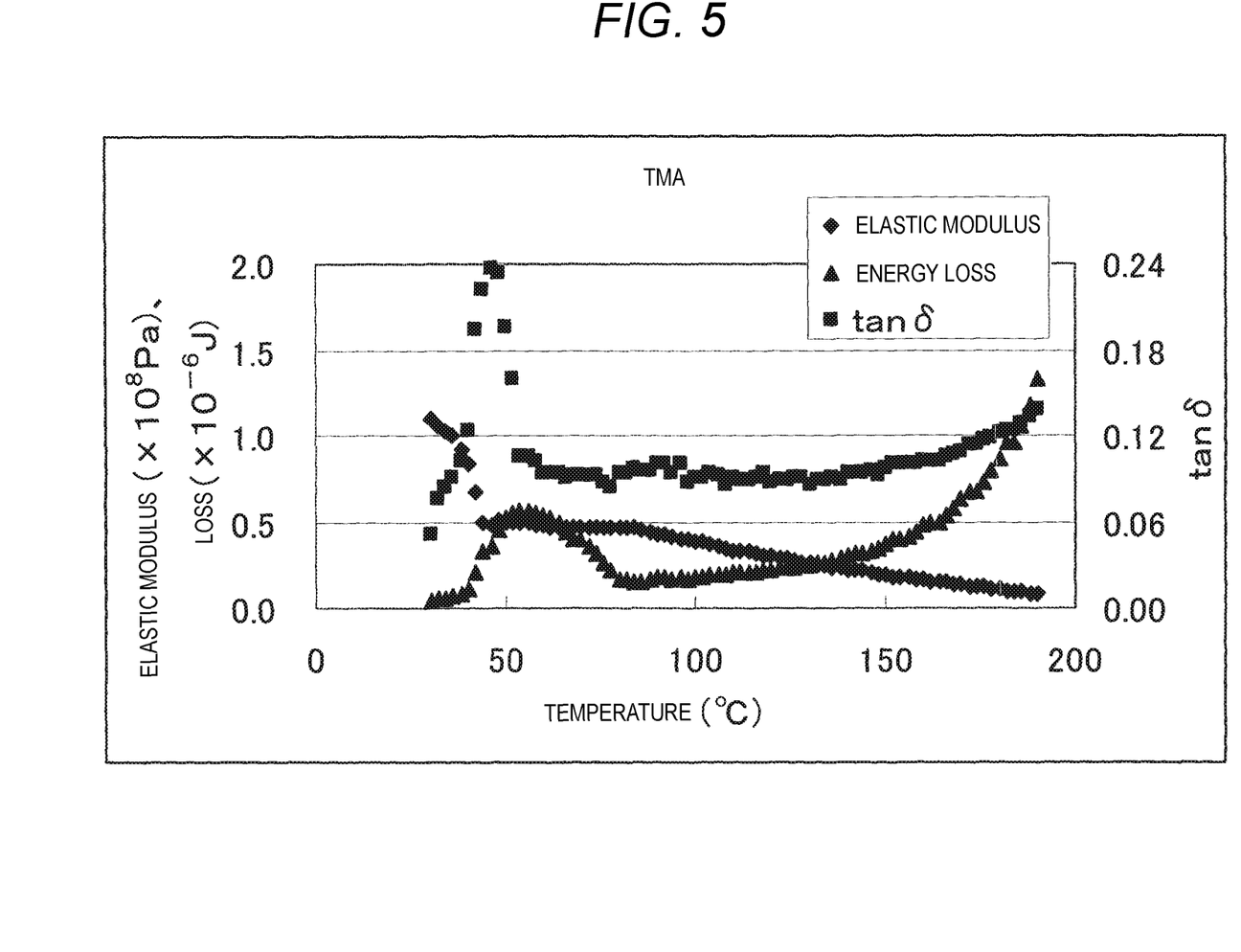
FIG. 5 is a graph showing a viscoelasticity of the tube of Example 3.

| Fluorine Resin(1) | Fluorine Resin(2) | ΔE loss (μJ) | Elastic Modulus at 50° C. (MPa) | Corresponding FIGS. |
|---|---|---|---|---|
| FEP-130J (98% by mass) | C-55AP (2% by mass) | 0.08 | 82 | |
| FEP-130J (80% by mass) | C-55AP (20% by mass) | 0.06 | 83 | FIG. 3 |
| FEP-NP120 (98% by mass) | C-55AP (2% by mass) | 0.03 | 83 | |
| FEP-NP120 (80% by mass) | C-55AP (20% by mass) | 0.02 | 159 | |
| FEP-100J (97% by mass) | C-88AX (3% by mass) | −0.51 | 60 | FIG. 4 |
| FEP-100J (90% by mass) | C-88AX (10% by mass) | −0.52 | 60 | |
| THV (98% by mass) | KYNAR740 (2% by mass) | 0.29 | 50 | FIG. 5 |
| THV (70% by mass) | KYNAR740 (30% by mass) | 0.26 | 52 | |

INDUSTRIAL APPLICABILITY

Since the tearable tube made of the fluorine resin of the present invention has an excellent tearability and heat-shrinkability, the tube may be mounted tightly on a mounting member when the tube is provided in a device, and may be excellent in handlability. Further, since the tearable tube made of the fluorine resin of the present invention may be manufactured by melt-extruding a raw material blended with different kinds of thermoplastic fluorine resins, it is possible to provide a tearable tube made of the fluorine resin which is able to be easily produced and has a stable tear characteristics.

The invention claimed is:

1. A heat-shrinkable tube having tearability, comprising at least a fluorine resin,
   wherein when a sine vibration stress with a cycle of 30 sec and an amplitude of 10 g is applied and a temperature is raised at rate of 5° C./min, an amount of change in loss energy, ΔE loss, with change in temperature from 175° C. to 185° C. is a positive value.

2. The heat-shrinkable tube having tearability of claim 1, wherein a storage elastic modulus at 50° C. is 100 MPa or less.

3. The heat-shrinkable tube having tearability of claim 1, wherein the fluorine resin contains at least a tetrafluoroethylene and a hexafluoropropylene as constituent monomer units.

4. The heat-shrinkable tube having tearability of claim 1, wherein the fluorine resin is a polymer made of at least three kinds of monomers and contains at least a tetrafluoroethylene and a hexafluoropropylene as constituent monomer units.

5. The heat-shrinkable tube having tearability of claim 1, wherein the fluorine resin contains at least a tetrafluoroethylene, a hexafluoropropylene and a perfluoroalkylvinyl ether as constituent monomer units.

6. The heat-shrinkable tube having tearability of claim 1, wherein the fluorine resin contains at least a tetrafluoroethylene, a hexafluoropropylene and a vinylidene fluoride as constituent monomer units.

7. The heat-shrinkable tube having tearability of claim 6, wherein the fluorine resin has a glass transition temperature of 40° C. or higher.

* * * * *

UNITED STATES PATENT AND TRADEMARK OFFICE
CERTIFICATE OF CORRECTION

| | | |
|---|---|---|
| PATENT NO. | : 9,623,154 B2 | Page 1 of 1 |
| APPLICATION NO. | : 15/205560 | |
| DATED | : April 18, 2017 | |
| INVENTOR(S) | : Masahiro Suzuki | |

It is certified that error appears in the above-identified patent and that said Letters Patent is hereby corrected as shown below:

On the Title Page

Column 1, Item (30) Foreign Application Priority Data, Line 2, delete "2011-245074" and insert -- 2011-254074 --

Signed and Sealed this
First Day of August, 2017

Joseph Matal
*Performing the Functions and Duties of the*
*Under Secretary of Commerce for Intellectual Property and*
*Director of the United States Patent and Trademark Office*